United States Patent [19]

Iseli

[11] Patent Number: Plant 5,948

[45] Date of Patent: Apr. 21, 1987

[54] JUNIPER PLANT NAMED 'MOTHER LODE'

[75] Inventor: Jean Iseli, Boring, Oreg.

[73] Assignee: Iseli Nursery, Inc., Boring, Oreg.

[21] Appl. No.: 709,765

[22] Filed: Mar. 8, 1985

[51] Int. Cl.[4] ..... A01H 5/00
[52] U.S. Cl. ..... Plt./50
[58] Field of Search ..... Plt./50

[56] References Cited

U.S. PATENT DOCUMENTS

P.P. 5,014 3/1983 Girard ..... Plt./50
P.P. 5,488 6/1985 Liddle ..... Plt./50

*Primary Examiner*—James R. Feyrer
*Attorney, Agent, or Firm*—Chernoff, Vilhauer, McClung & Stenzel

[57] ABSTRACT

A new and distinct *Juniperus horizontalis* which was discovered as a sport on a Wiltonii Juniper is characterized by its bright yellow lemon color which turns to a bronze yellow during the Winter.

2 Drawing Figures

BACKGROUND AND SUMMARY OF THE INVENTION

The present invention relates to a new and distinct variety of ornamental plant of the Cupressaceae family and more specifically to a plant of the *Juniperus horizontalis* genera which is marketed under the variety name "Mother Lode."

The new variety was discovered by me as a sport on a Wiltonii Juniper at Iseli Nurseries at 15241 S.E. Tickle Creek Road, Boring, Oreg. in May of 1980.

The primary feature of this new variety which connotates its distinctive advantage over existing types are its bright lemon yellow color which becomes intense during the summer and turns to a bronze yellow during the winter.

Asexual reproduction of my new and distinct variety through grafting and by vegetative cuttings shows that its unique combination of characteristics come true to form and are established and transmitted through succeeding generations.

BRIEF DESCRIPTION OF THE DRAWINGS

The accompanying photographs show typical specimens of the vegetative growth of the new variety in different stages of development and are depicted in color as nearly true as is reasonably possible to make the same in color illustrations of this character.

DETAILED DESCRIPTION OF THE PLANT

Figure 1:
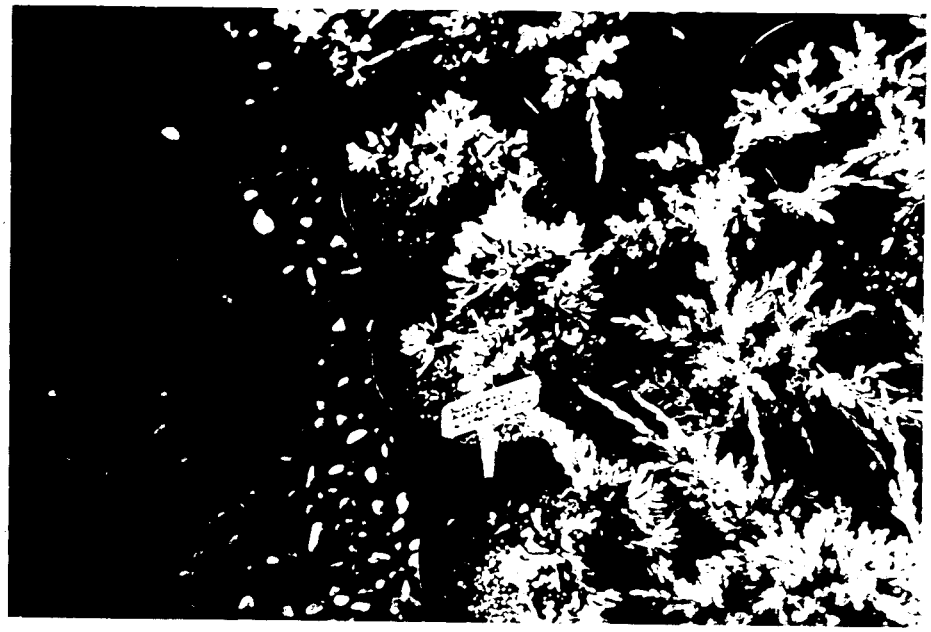
FIG. 1 shows the plant of the subject invention alongside of the *Juniperus horizontalis wiltonii* on which it was discovered.
Figure 2:
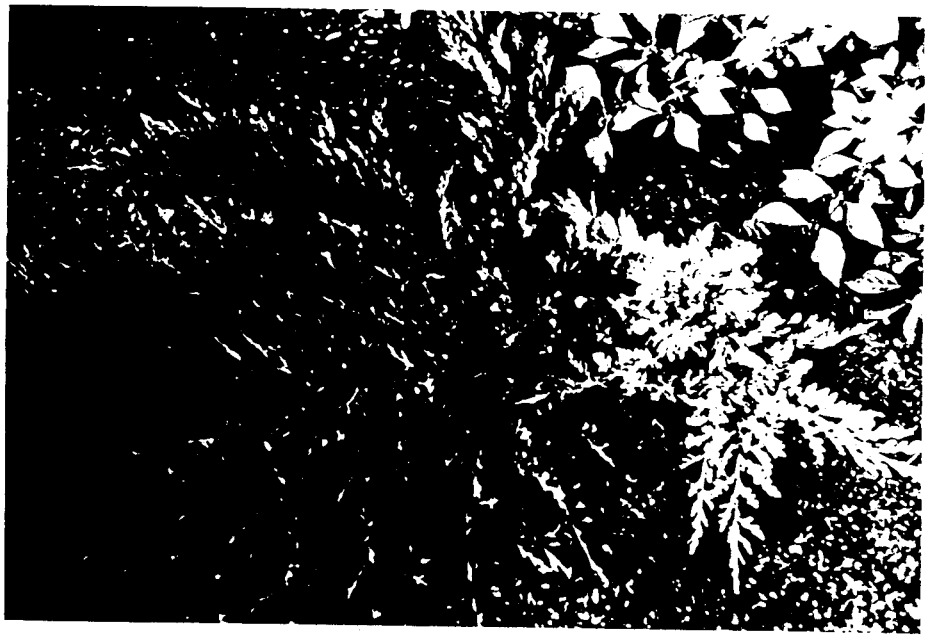
FIG. 2 show two-year-old plants at the height of their color.

The following is a detailed description of the new and distinct variety. To help in the identification of the colors, the *Naturalist's Color Guide* by Frank B. Smithe, obtainable from the American Museum of Natural History has been followed.

Branch and Foliage Description

Branches totally procumbent, thin, less than 1.5 mm thick, annual growth between 18 and 25 cm, maximum lateral branch growth between 5 and 7 cm, lateral branches ascending at 30° and inclined forward at 145° from the stem. Leaves very small, adpressed, young needles sulphur yellow (Y 8.0/6.0) in Spring and Summer turning to orange yellow (YR 8.0/14.0) in Fall and Winter. Two year old needles and stem color (aside from the leaves described above) are identical to the parent, *Juniperus horizontalis wiltonii.*

Size, Characteristics

At ten years, plant is less than 10 cm in height with a maximum width of 250 cm. Sizes given are projections based on current growth rates on 6 to 7 year old plants. In Oregon, the plant is somewhat slow growing for the first several years and thereafter the growth begins to accelerate. It cannot be considered a dwarf plant as it is sometimes represented.

Leaves (Needles)

On main stem, leaves are less than 1 cm in length. Branches are spaced less than 2 cm apart and emerge from stem in alternating pattern, first one side and then the next. Branchlets are smaller versions of branches and spaced less than 0.05 cm apart with branchlet leaves less than 0.020 cm in length. To my eye, the plant foliage appears adult in nature, and juvenile growth, as would be seen in Juniperus Sabina Broadmore for example, is not in evidence.

Texture

Branches have a soft touch with a slight prickliness from addressed leaves (needles) along the stem.

Growth Habit

Plant is prostrate spreading with stems uniformly radiating from the crown, dense in appearance with current years' growth radiating outward from dense center.

Hardiness

Plant is quite hardy in USDA Zone 4 and has withstood Summer heat above 105° Fahrenheit without burning or scorching.

In a comparison of specimens of 'Mother Lode' with the parent *Juniperus horizontalis wiltonii* taken in late December 1985 using The *R.H.S. Colour Chart* the following distinguishing characteristics were observed:

Leaves: The newest leaves of 'Mother Lode' were R.H.S. Green-Yellow Group 1A–B, progressing uniformly to R.H.S. Yellow-Green Group 146-A–D a distance of 9–12 cm from the terminals. Leaves of the parent were a generally uniform R.H.S. Green Group 137C with some areas under moderate bloom near R.H.S. 136D–138C.

Stems: Green stem portions of 'Mother Lode' ranged from Yellow-Green Group 145A–154C while the corresponding stem portions of the parent were more uniformly 145A–B. Brown stem portions were R.H.S. Greyed-Orange Group 173A–D for both plants.

Bloom: Bloom on leaves of 'Mother Lode' was very slight and inconspicuous; that of the parent slight to moderate, the bloom on the old leaves of both parents near R.H.S. Green Group 138D apparently rendering the characteristic blue hue to both plants, but more predominantly in the parent plant.

Branching: The branching of 'Mother Lode' is more condensed along the stems giving a more flushed and compacted appearance when compared to the parent, which has stems with fewer more widely spaced lateral breaks. The leaf scales at the base of the green stem portion being a more squat 7–9 mm on 'Mother Lode' compared to about 9–12 mm for scales at the same location on the parent plant's stem.

I claim:

1. A new and distinct variety of *Juniperus horizontalis* plant, substantially as described and illustrated, obtained as a sport from *Juniperus horizontalis wiltonii* characterized by its lemon yellow new growth which turns bronze yellow during the winter.

* * * * *

UNITED STATES PATENT AND TRADEMARK OFFICE

CERTIFICATE OF CORRECTION

PATENT NO. : Plant 5,948

DATED : April 21, 1987

INVENTOR(S) : Jean Iseli

It is certified that error appears in the above-identified patent and that said Letters Patent is hereby corrected as shown below:

Col. 2, Line 31 Change "addressed" to --adpressed--

Signed and Sealed this

Seventeenth Day of November, 1987

*Attest:*

DONALD J. QUIGG

*Attesting Officer*

*Commissioner of Patents and Trademarks*